United States Patent [19]

Arndt et al.

[11] 4,128,413

[45] Dec. 5, 1978

[54] CARBANILIC ACID ESTERS AND HERBICIDAL COMPOSITION CONTAINING SAME

[75] Inventors: Friedrich Arndt; Gerhard Boroschewski, both of Berlin, Fed. Rep. of Germany

[73] Assignee: Schering Aktiengesellschaft, Berlin and Bergkamen, Fed. Rep. of Germany

[21] Appl. No.: 809,935

[22] Filed: Jun. 24, 1977

[30] Foreign Application Priority Data

Jul. 2, 1976 [DE] Fed. Rep. of Germany ....... 2630418

[51] Int. Cl.$^2$ .......................... A01N 9/12; A01N 9/20; C07C 121/78; C07C 154/155
[52] U.S. Cl. .......................................... 71/100; 71/98; 71/105; 260/455 A; 260/465 D
[58] Field of Search ..................... 260/465 D, 455 A; 71/100, 105, 111, 98

[56] References Cited

U.S. PATENT DOCUMENTS

| | | | |
|---|---|---|---|
| 3,404,975 | 10/1968 | Wilson et al. | 71/100 |
| 3,551,477 | 12/1970 | Koenig et al. | 260/465 D X |
| 3,904,396 | 9/1975 | Boroschewski et al. | 71/111 |

*Primary Examiner*—Dolph H. Torrence
*Attorney, Agent, or Firm*—Michael J. Striker

[57] ABSTRACT

Carbanilic acid ester of the formula

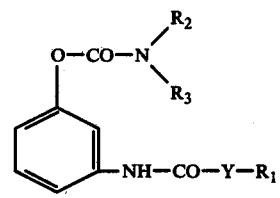

in which
$R_1$ is an aliphatic hydrocarbon residue which may also be substituted,
$R_2$ is a cyanoalkyl residue,
$R_3$ is an aromatic hydrocarbon residue which may also be substituted and
Y is oxygen or sulfur.

The compounds are herbicidal agents with a broad spectrum of activity and of particular compatibility regarding cotton and other plantation cultures.

55 Claims, No Drawings

CARBANILIC ACID ESTERS AND HERBICIDAL COMPOSITION CONTAINING SAME

BACKGROUND OF THE INVENTION

The invention relates to carbanilic acid esters and a process of making the same.

The herbicidal activity of diurethanes is known (German Pat. No. 1,567,151). These agents, however, have only an unsatisfactory breadth of activity since they are without effect against certain important weeds. Besides, so far a good herbicidal activity against grass-type weeds has not been found, neither in preemergence nor postemergence application. These herbicides of the prior art, furthermore, have no specific compatibility with cotton and other plantation cultures and cannot readily be used in such agricultural areas.

It is therefore an object of the present invention to provide for a herbicidal agent which has a broad spectrum of activity against monocotyl- and dicotyl-weeds and is specifically highly compatible with cotton and other agricultural plants.

SUMMARY OF THE INVENTION

This object is met by a herbicidal agent which comprises at least one compound of the formula

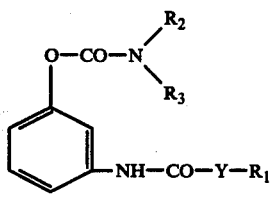

in which
  $R_1$ is an aliphatic hydrocarbon residue which may also be substituted,
  $R_2$ is a cyanoalkyl residue,
  $R_3$ is an aromatic hydrocarbon residue which may also be substituted and
  Y is oxygen or sulfur.

Among the compounds of the invention those have a superior spectrum of activity and selectivity in which
  $R_1$ is alkyl of 1 to 6 carbon atoms, alkenyl of 2 to 6 carbon atoms or alkinyl of 2 to 6 carbon atoms,
  $R_2$ is a cyanoalkyl group of 1 to 4 carbon alkyl
  $R_3$ is phenyl which may also be substituted in one or two places by the same or different substituents selected from the group consisting of alkyl of 1 to 6 carbon atoms, alkoxy of 1 to 6 carbon atoms, alkylthio of 1 to 3 carbon atoms, halogen or trifluoromethyl, and
  Y is oxygen or sulfur.

A particularly effective compound is N-(2-cyanoethyl)-carbanilic acid (3-(methoxycarbonylamino)-phenyl)ester.

The compounds of the invention surprisingly are broadly effective against a multiplicity of undesirable plants of which the following are only mentioned for illustration:

Gramineae
Festuca sp., Alopecurus sp., Agrostis sp., Avena sp., Echinochloa, Setaria sp., Sorghum sp., Poa sp., Lolium sp., Arrhenaterum sp., Phalaris sp., Phleum sp., Eleusine sp., Bromus sp., Hordeum sp. and others.

Cyperaceae
Cyperus sp. and others.

Liliaceae
Allium sp. and others.

Amaranthaceae
Amaranthus sp., and others.

Boraginaceae
Anchusa sp., Amsinckia sp., Myosotis sp. and others.

Caryophylaceae
Stellaria sp., Spergula sp., Gerastium sp. and others.

Chenopodiaceae
Chenopodium sp., *Salsola kali*, Atriplex sp., Kochia sp. and others.

Convoloulaceae
Ipomea sp. and others.

Compositae
Ambrosia sp., Lactuca sp., Senecio sp., Xanthium sp., Galinsoga sp., Centaurea sp., Matricaria sp., Helianthus sp., Chrysanthemum sp., *Cichorium intybus* and others.

Cruciferae
Brassica sp., *Cheiranthus cheiri*, Capsella sp., Thlaspi sp., Sinapis sp. and others.

Labiatae
Lamium sp., Galeopsis sp. and others.

Leguminosae
Medicago sp., Trifolium sp., Vicia sp., Cassia sp. and others.

Malvaceae
*Abutilon theophrasti*, Sida sp., Hibiscus sp. and others.

Papaveraceae
Papaver sp. and others.

Polygonaceae
Polygonum sp. and others.

Portulacaceae
Portulaca sp. and others.

Rubiaceae
Galium sp., Richardia sp. and others.

Ranunculaceae
Delphinium sp., Adonis sp. and others.

Scrophulariaceae
Linaria sp., Digitalis sp., Veronica sp. and others.

Solanaceae
Datura sp., Solanum sp., Physalis sp. and others.

Urticaceae
Urtica sp. and others.

Umbelliferae

*Daucus carota* and others.

The application against these various weeds can be effected both in a preemergence and postemergence use. A particular advantage is that the compounds of the invention are highly compatible specifically for agricultural plantations such as cotton and other plantations.

It has also been found that the herbicidal activity of the compounds of the invention surprisingly can be substantially augmented if they are used with an amount of surface active agents which is greater than the normally used amounts of these additives in similar connections. Preferably, the surface active agents are used in a weight relation of 1:10 to 1:0.4 of active agent to surface active agent, and most preferably in a weight relation of 1:1 to 1:2.

The compounds of the invention can be used either alone or intermixed with each other or a mixture with other agents. Depending on the particular purpose, for instance the following herbicidal compounds may be used with the compounds of the invention. The added compounds may be incorporated only immediately prior to use of the compounds of the invention. These additives broadly comprise the following groups:
  substituted anilines,
  substituted aryloxycarboxylic acids and their salts, esters and amides,
  substituted ethers,
  substituted arsonic acids and their salts, esters and amides,
  substituted benzimidazoles,
  substituted benzisothiazoles,
  substituted benzthiadiazinone dioxides,
  substituted benzoxazines,
  substituted benzoxazinones,
  substituted benzthiazoles,
  substituted benzthiadiazoles,
  substituted biurets,
  substituted quinolines,
  substituted carbamates,
  substituted aliphatic carboxylic acids and their salts, esters and amides,
  substituted aromatic carboxylic acids and their salts, esters and amides,
  substituted carbamoylalkyl-thio- or dithiophosphates
  substituted quinazolines,
  substituted cycloalkylamidocarbonylthiol acids and their salts, esters and amides,
  substituted cycloalkylcarbonylamido-thiazoles,
  substituted dicarboxylic acids and their salts, esters and amides,
  substituted dihydrobenzofuranylsulfonates,
  substituted disulfides,
  substituted dipyridylium salts,
  substituted dithiocarbamates,
  substituted dithiophosphoric acids and their salts, esters and amides,
  substituted urea derivatives,
  substituted hexahydro-1H-carbothioates,
  substituted hydantoines,
  substituted hydrazides,
  substituted hydrazonium salts,
  substituted isoxazolpyrimidones,
  substituted imidazoles,
  substituted isothiazolpyrimidones,
  substituted ketones,
  substituted naphthoquinones,
  substituted aliphatic nitriles,
  substituted aromatic nitriles,
  substituted oxadiazoles,
  substituted oxadiazinons,
  substituted oxadiazolidindiones,
  substituted oxadiazinediones,
  substituted phenols and their salts and esters,
  substituted phosphonic acids and their salts, esters and amides,
  substituted phosphoniumchlorides,
  substituted phosphonalkylglycines,
  substituted phosphites,
  substituted phosphoric acids and their salts, ester and amides,
  substituted piperidines,
  substituted pyrazoles,
  substituted pyrazolalkylcarboxylic acids and their salts, esters, and amides,
  substituted pyrazolium salts,
  substituted pyrazoliumalkylsulfates,
  substituted pyridazines,
  substituted pyridazones,
  substituted pyridine-carbonic acids and their salts, esters and amides,
  substituted pyridines,
  substituted pyridinecarboxylates,
  substituted pyridinone,
  substituted pyrimidone,
  substituted pyrrolidine-carboxylic acids and their salts, esters and amides,
  substituted pyrrolidines,
  substituted arylsulfonic acids and their salts, esters and amides,
  substituted styrenes,
  substituted tetrahydro-oxadiazindiones,
  substituted tetrahydromethanoindenes,
  substituted tetrahydro-diazol-thiones,
  substituted tetrahydro-thiadiazine-thiones,
  substituted tetrahydro-thiadiazolediones,
  substituted thiadiazoles,
  substituted aromatic thiocarboxylic acid amides,
  substituted thiocarboxylic acids and their salts, esters and amides,
  substituted thiolcarbamates,
  substituted thiophosphoric acids and their salts, esters and amides,
  substituted triazines,
  substituted triazoles
  substituted uracils, and
  substituted urethidindiones.

Among these broad groups the following compounds are particularly suited as additives:
  4-(1,1-dimethylethyl-2,6-dinitro-N-(1-methylpropyl)-aniline,
  $N^4$, $N^4$-diethyl-$\alpha,\alpha,\alpha$-trifluoro-3,5-dinitrotoluene-2,4-diamine,
  2,2-dichloropropionic acid,
  4-(methylsulfonyl)-2,6-dinitro-N,N-dipropylaniline,
  $\alpha,\alpha,\alpha$-trifluoro-2,6-dinitro-N,N-dipropyl-p-toluidine,
  3-(3,4-dichlorophenyl)-1,1-dimethylurea,
  1,1-dimethyl-3-($\alpha,\alpha,\alpha$-trifluoro-m-tolyl)-urea,
  3-tetrafluoroethoxyphenyl-N,N-dimethyl-urea,
  2,4-bis-(isopropylamino)-6-(methylthio)-s-triazine,
  mono-sodium-methanarsonate,
  di-sodium methanarsonate,
  herbicidal oils (naphtha),
  3-(3,4-dichlorophenyl)-1-methoxy-1-methyl-urea, 4-phenylsulfonyl-trifluoromethansulfono-o-toluidine,
trichloroacetic acid,
sodium and potassium azide,
1,1'-dimethyl-4,4'-bipyridilium-salt
5-chloro-3-(2-tetrahydropyranyl)-6-methyluracil,
3-(4-bromo-3-chlorophenyl)-1-methoxy-1-methylurea,
3-(p-chlorophenyl)-1,1-dimethylurea,
3-(hexahydro-4,7-methanoindan-5-yl)-1,1-dimethylurea,
2-ethylthio-4,6-bis-(isopropylamino)-s-triazine,
dimethyl-tetrachloro-terephthalate,
2-sec.butyl-4,6-dinitrophenol,
N,N-dimethyl-2,2-diphenylacetamide,
N-propyl-N-(2-chloroethyl)-$\alpha,\alpha,\alpha$-trifluoro-2,6-dinitro-p-toluidine,
N-n-propyl-N-cyclopropylmethyl-4-trifluoromethyl-2,6-dinitroaniline,
N-sec.butyl-2,6-dinitro-3,4-xylidine,
N-sec.butyl-4-tert.butyl-2,6-dinitro-aniline,
1,1-dimethyl-3-(m-chloro-p-trifluoromethoxy-phenyl)-urea,
methyl-5-(2',4'-dichlorophenoxy)-2-nitro-benzoate,
2-(3,4-dichlorophenyl)-4-methyl-1,2,4-oxadiazolidine-3,5-dione,
N-(1-ethylpropyl)-2,6-dinitro-3,4-xylidine,
N-1-naphthylphthalamic acid,
2-[(4-chloro-6-ethylamino-s-triazine-2-yl)-amino]-2-methylpropionitrile,
4-chloro-5-(methylamino)-2-($\alpha,\alpha,\alpha$-trifluoro-m-tolyl)-3-(2H)-pyridazinone,
2-chloro-2',6'-diethyl-N-(methoxymethyl)-acetanilide,
N-(phosphonomethyl)-glycine,
3,5-dinitro-$N^4$, $N^4$-dipropyl-sulfanilamide,
r-2-ethyl-5-methyl-c-5-(2-methylbenzyloxy)-1,3-dioxane,
c-5-(2-chlorobenzyloxy)-r-2-ethyl-5-methyl-1,3-dioxane,
N-chloroacetyl-N-(2,6-diethylphenyl)-glycinethylester,
2-(1-allyloxyamino)-butylidene-5,5-dimethyl-4-methoxycarbonyl-cyclohexane-1,3-dione,
(1-methylethyl)-phosphoramidothioate,
2-[4-(4-chlorophenoxy)-phenoxy]-propionic acid isobutylester,
2-[4-(2,4-dichlorophenoxy)-phenoxy]-propionic acid methylester,
$N^3$, $N^3$-di-n-propyl-2,4-dinitro-6-trifluoromethyl-m-phenylenediamine,
2-ethoxy-2,3-dihydro-3,3-dimethyl-5-benzofuranylmethansulfonate,
c-5-(2-chlorobenzyloxy)-r-2-isopropyl-5-methyl-1,3-dioxane, and
r-2-isopropyl-5-methyl-c-5-(2-methylbenzyloxy)-1,3-dioxane.

There can also be used other additives, for instance non-phytotoxic additives which, with herbicides, result in a synergistic increase of activity such as wetting agents, emulsifying agents, solvents, and oily additives.

It is preferred to use the active agents of the invention or their mixture in the form of compositions such as powders, dusting agents, granulates, solutions, emulsions or suspensions and upon addition of liquid and/or solid carrier materials or diluents and, if desired, wetting, adhesion, emulsion and/or dispersion improving agents.

Suitable liquid carrier materials are, for instance, water, aliphatic and aromatic hydrocarbons, such as, benzene, toluene, xylene, cyclohexanone, isophorone, dimethylsulfoxide, dimethylformamide, and further mineral oil fractions and acetic acid.

As solid carrier materials mineral earths are suited, for instance, tonsil, silica gel, talc, kaolin, attaclay, limestone, silicic acid, and plant products, for instance flours.

As examples of surface active agents there may be mentioned calciumlignosulfonate, polyoxyethylenealkylphenylether, naphthalinesulfonic acids and their salts, phenolsulfonic acids and their salts, formaldehyde condensation products, fatty alcoholsulfates and substituted benzene sulfonic acids and their salts.

The amount of active agent or agents in the different compositions can be varied within broad limits. The compositions may, for instance, include between about 10 and 80% by weight of active agents, about 90 to 20% by weight of liquid or solid carrier materials as well as, if desired, up to 20% by weight of surface active agents.

The application of the compositions can be effected can be effected as conventional, for instance with water as carrier material in spray amounts of about 100 to 1000 liters per about 2.5 acres. The application is possible in the so-called "low-volume" and "ultra-low-volume" process and also in form of so-called micro granulates.

The compounds of the inventions may be made in different ways.

I. Compounds of the formula

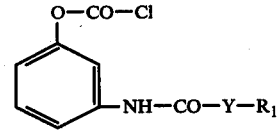

are reacted with amines of the formula

in the presence of an acid acceptor, for instance in the form of an excess of amine or of an inorganic base such as sodium hydroxide, sodium carbonate, potassium carbonate, or a tertiary organic base like triethylamine. $R_1$ to $R_3$ and Y in this connection have the same meaning as in the above formula of the final compound.

II. Another process for making the compounds of the invention consists in reacting compounds of the formula

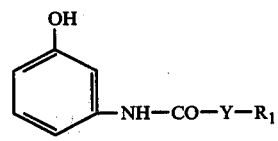

in the presence of a tertiary organic base such as triethylamine or pyridine or in the form of an alkali salt such as sodium or potassium salt, with a carbamoylchloride of the formula

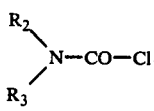

The reaction at I and II may be carried out at a temperature of about 0° to 100° C. upon use of suitable solvents. The final products may be isolated in conventional form. $R_1$, $R_2$ and $R_3$ as well as Y have the same meaning as in the final compound also in the process II above.

The following example illustrates the making of a compound of the invention.

EXAMPLE 1

N-(2-cyanoethyl)carbanilic acid-[3-(methoxycarbonylamino)phenyl]-ester

A solution of 43.9 g of 3-anilinopropionic acid nitrile in 100 ml acetic acid ethylester is reacted with 100 ml water. A solution of 68.7 g of chloroformic acid-3-methoxycarbonylamino-phenyl ester in 250 ml of acetic acid ethylester is then added dropwise within a period of 25 minutes simultaneously with a solution of 41.4 g of potassium carbonate in 250 ml water while the reaction is stirred and cooled to about 10° to 14° C. Thereafter the stirring is continued for 30 minutes at 10° C. The organic phase is then separated and washed at 0° C. with dilute sodium hydroxide, dilute hydrochloric acid and water. After drying with magnesium sulfate the mass is concentrated by evporation in a partial vacuum. The oily residue crystallizes from ether. The yield was 76.6 g = 75% of the theoretical value. m.p. 98°–99° C.

Analysis: theoretical: C: 63.71, H: 5.05, N: 12.38%; obtained: C: 63.98, H: 5.65, N: 12.19%.

In an analagous manner the following compounds have been made:

| Ex. | Compound | Physical constants |
|---|---|---|
| 2 | N-cyanomethylcarbanilic acid-(3-(methoxy-carbonylamino)-phenyl)- | m.p. 111 – 113° C |
| 3 | N-(2-cyanoethyl)-carbanilic acid-(3-(ethoxycarbonylamino)-phenyl)-ester | m.p. 86 – 88° C |
| 4 | N-cyanomethylcarbanilic acid-(3-(ethoxy-carbonylamino)-phenyl)-ester | m.p. 122 – 24° C |
| 5 | N-(2-cyanoethyl)-carbanilic acid-(3-(1-methylethoxycarbonylamino)-phenyl)-ester | m.p. 107 – 109° C |
| 6 | N-cyanomethylcarbanilic acid-(3-1-methylethoxycarbonylamino)-phenyl)-ester | m.p. 141 – 142° C |
| 7 | N-cyanomethylcarbanilic acid-(3-methylthiocarbonylamino)-phenyl)-ester | m.p. 136 – 138°C |
| 8 | N-(2-cyanoethyl)-carbanilic acid-(3-(methylthiocarbonylamino)-phenyl)-ester | m.p. 123 – 125° C |
| 9 | N-(2-cyanoethyl)-carbanilic acid-(3-(1-methylpropoxycarbonylamino)-phenyl)-ester | m.p. 78 – 80° C |
| 10 | N-cyanomethyl-3-trifluoromethyl-carbanilic acid-(3-methoxycarbonylamino)-phenyl)-ester | m.p. 158 – 160° C |
| 11 | N-(2-cyanoethyl)-carbanilic acid-(3-(allyloxycarbonylamino)-phenyl)-ester | m.p. 84 – 86° C |
| 12 | N-(2-cyanoethyl)-carbanilic acid-(3-(2-propinyloxycarbonylamino)-phenyl)-ester | m.p. 108 – 111° C |
| 13 | N-(2-cyanoethyl)-3-methoxycarbanilic acid-(3-(methoxycarbonylamino)-phenyl)-ester | m.p. 87 – 88° C |
| 14 | N-cyanomethyl-3,5-dichlorocarbanilic acid-(3-(methoxycabonylamino)-phenyl)-ester | m.p. 150 – 152° C |
| 15 | N-cyanomethyl-3,4-dichlorocarbanilic acid-(3-methoxycarbonylamino)-phenyl)-ester | m.p. 112 – 114° C |
| 16 | N-(2-cyanoethyl)-4-ethylcarbanilic acid-(3-(methoxycarbonylamio)-phenyl)-ester | $n_D^{20} = 1,5425$ |
| 17 | N-(2-cyanoethyl)-3-chloro-4-methyl-carbanilic acid-(3-methoxycarbonyl-amino)-phenyl)-ester | m.p. 104 – 105° C |
| 18 | N-(2-cyanoethyl)-4-bromocarbanilic acid-(3-(methoxycarbonylamino)-phenyl)-ester | m.p. 111 – 113° C |
| 19 | 4-ethyl-N-(2-cyanoethyl)-carbanilic acid-[3-(ethoxycarbonylamino)-phenyl]-ester | m.p. 80 – 82° C |
| 20 | N-(2-cyanoethyl)-3-methoxycarbonyl-amino)-phenyl]-ester | m.p. 67 – 69° C |
| 21 | N-(2-cyanoethyl)-carbanilic acid-[3-(2-chloro-1-methylethoxy-carbonyl-amino)-phenyl]-ester | m.p. 112 – 115° C |
| 22 | N-(2-cyanoethyl)-carbanilic acid [3-(n-propoxycabonylamino)-phenyl]-ester | m.p. 101 – 103° C |
| 23 | N-(2-cyanoethyl)-4-ethylcarbanilic-acid-[3-(2-methoxy-ethoxy-carbonyl-amino)-phenyl]-ester | m.p. 68 – 70° C |
| 24 | N-(2-cyanoethyl)-3-methoxycarbanilic acid-[3-(1-methyl-ethoxycarbonylamino)-phenyl]-ester | m.p. 110 – 113° C |
| 25 | 4-ethyl-N-(2-cyanoethyl)-carbanilic acid-[3-(isopropoxycarbonylamino)-phenyl]-ester | m.p. 107 – 108 ° C |
| 26 | N-(2-cyanoethyl)-2-methoxycarbanilic acid-[3-(methoxycarbonylamino)-phenyl]-ester | m.p. 99 – 101° C |
| 27 | N-(2-cyanoethyl)-4-ethylcarbanilic acid-[3-butoxycarbonylamino)-phenyl]-ester | m.p. 70° C |
| 28 | N-(2-cyanoethyl)-3-methoxycarbanilic acid-[3-(methylthiocarbonylamino)-phenyl]-ester | m.p. 68 – 70° C |
| 29 | N-(2-cyanoethyl)-3-methylcarbanilic acid-[3-(methoxycarbonylamino)-phenyl]-ester | m.p. 96 – 99° C |
| 30 | N-(2-cyanoethyl)-carbanilic acid-[3-(2-chloro-1-methylethoxycarbonyl-amino)-phenyl]-ester | $n_D^{20} = 1,5460$ |
| 31 | N-(2-cyanoethyl)-carbanilic acid-[3-(methoxy-ethoxycarbonylamino-phenyl]-ester | $n_D^{20} = 1,5268$ |
| 32 | 3-chloro-N-(2-cyanoethyl)-4-methyl-carbanilic acid-[3-(ethoxycarbonyl-amino)-phenyl]-ester | m.p. 118 – 120° C |
| 33 | N-(2-cyanoethyl)-3-methoxycarbanilic acid-[3-(allyloxycarbonylamino)-phenyl]-ester | m.p. 85 – 88° C |
| 34 | N-(2-cyanoethyl)-4-methylcarbanilic acid-[3-(2-propinyloxycarbonylamino)-phenyl]-ester | m.p. 120° C |
| 35 | N-(2-cyanoethyl)-4-methylcarbanilic acid-[3-(isopropoxycabonylamino-phenyl]-ester | m.p. 112 – 113° C |
| 36 | N-(2-cyanoethyl)-3-methoxycarbanilic acid-[3-(2-propinyloxycarbonylamino)-phenyl]-ester | m.p. 111 – 112° C |
| 37 | N-cyanomethyl-3-methylcarbanilic acid-[3-(methoxycarbonylamino)-phenyl]-ester | m.p. 103 – 105° C |
| 38 | N-(2-cyanoethyl)-3-methoxycarbanilic acid-[3-(2-methoxyethoxycarbonylamino)-phenyl]-ester | m.p. 78 – 80° C |
| 39 | N-cyanomethyl-3-methylcarbanilic acid-[3-(ethoxycarbonylamino)-phenyl]]-ester | m.p. 94 – 96° C |
| 40 | N-(2-cyanoethyl)-4-methylcarbanilic acid-[3-(sek-butyloxycabonylamino)-phenyl]-ester | m.p. 74 – 76° C |
| 41 | 3-chloro-N-(2-cyanoethylcarbanilic acid-[3-methoxycarbonylamino)-phenyl]-ester | m.p. 148 – 150° C |
| 42 | N-cyanomethyl-2,6-dimethylcarbanlic acid-[3-(methoxycarbonylamino)-phenyl]-ester | m.p. 147 – 149° C |
| 43 | N-cyanomethyl-2,6-dimethylcarbanilic acid-[3-(ethoxycarbonylamino)-phenyl]-ester | m.p. 151 – 153° C |
| 44 | N-cyanomethyl-3-methylcarbanilic acid-[3-isopropoxycarbonylamino)-phenyl) -ester | m.p. 129 – 131° C |
| 45 | N-cyanomethyl-3-methylcaranilic acid-[3-(2-propinyloxycarbonylamino)-phenyl]-ester | m.p. 93 – 95° C |
| 46 | 4-ethyl-N-(2-cyanoethyl)-carbanilic acid-[3-(methoxycarbonylamino)-phenyl]-ester | $n_D^{20} = 1,5465$ |

-continued

| Ex. | Compound | Physical constants |
|---|---|---|
| 47 | N-cyanomethyl-2,3-dimethyl-carbanilic acid-[3-(methoxycarbonylamino)-phenyl]-ester | m.p. 114 – 116° C |
| 48 | N-cyanomethyl-3,4-dimethylcarbanilic acid-[3-(methoxycarbonylamino)-phenyl]-ester | m.p. 83 – 85° C |
| 49 | N-cyanomethyl-3,5-dimethylcarbanilic acid-[3-(methoxycarbonylamino)-phenyl]-ester | m.p. 106 – 108° C |
| 50 | N-(2-cyanoethyl)-4-methylcarbanilic acid-[3-(2-methylpropoxycarbonylamino)-phenyl]-ester | m.p. 75° C |

These compounds are soluble, for instance in acetone, cyclohexanone, acetic acid ethylester, isophorone, tetrahydrofuran, dioxane, dimethylformamide, hexamethylphosphoric acid triamide. They are practically insoluble in water and light gasoline.

The following examples will explain the use of the compounds of the invention.

EXAMPLE A

The compounds listed below in Table I were applied by spraying to Sinapis and Solanum as test plants in preemergence and postemergence application in a hothouse. The amounts were 5 kg of active agent per about 2.5 acres emulsified in 600 liters of water for the same area.

Three weeks after application the results were evaluated on a scale from 0 = no effect, to 4 = total destruction of the plants. As appears from the following table normally destruction of the test plants was accomplished.

TABLE I

| Compound | Application | | | |
|---|---|---|---|---|
| | Preemergence | | Postemergence | |
| | Sinapis | Solanum | Sinapis | Solanum |
| N-cyanomethylcarbanilic acid-(3-(methoxycarbonylamino)-phenyl)-ester | 4 | 4 | 4 | 4 |
| N-(2-cyanoethyl)-carbanilic acid (3-methoxycarbonylamino)-phenyl)-ester | 4 | 4 | 4 | 4 |
| N-(2-cyanoethyl)-carbanilic acid-(3-ethoxycarbonylamino)-phenyl)-ester | 4 | 4 | 4 | 4 |
| N-cyanomethylcarbanilic acid-(3-ethoxycarbonylamino)-phenyl)-ester | 4 | 4 | 4 | 4 |
| N-(2-cyanoethyl)-carbanilic acid-(3-(1-methylethoxycarbonylamino)-phenyl)-ester | 4 | 4 | 4 | 4 |
| N-cyanomethylcarbanilic acid-(3-(1-methylethoxycarbonylamino)-phenyl)-ester | 4 | 4 | 4 | 4 |
| N-cyanomethylcarbanilic acid-(3-(methylthiocarbonylamino)-phenyl ester | 4 | 4 | 4 | 4 |
| N-(2-cyanoethyl)-carbanilic acid-(3-(methylthiocarbonylamino)-phenyl)-ester | 4 | 4 | 4 | 4 |
| N-(2-cyanoethyl)-carbanilic acid-(3-(1-methylpropoxycarbonylamino)-phenyl)-ester | 4 | 4 | 4 | 4 |
| N-cyanomethyl-3-trifluoromethyl-carbanilic acid-(3-(methoxycarbonylamino)-phenyl)-ester | 4 | 4 | 4 | 4 |
| N-(2-cyanoethyl)-carbanilic acid--(3-(allyloxycarbonylamino)-phenyl)-ester | 4 | 4 | 4 | 4 |
| N-(2-cyanoethyl)-carbanilic acid-(3-(2-propinyloxycarbonylamino)-phenyl)-ester | 4 | 4 | 4 | 4 |
| N-(2-cyanoethyl))-3-methoxycarbanilic acid-(3-methoxycarbonylamino)-phenyl)-ester | 4 | 4 | 4 | 4 |
| N-cyanomethyl-3,5-dichlorocarbanilic acid-(3-(methoxycarbonylamino)-phenyl)-ester | 4 | 4 | 4 | 4 |
| N-cyanomethyl-3,4-dichlorocarbanilic acid-(3-(methoxycarbonylamino)-phenyl)-ester | 4 | 4 | 4 | 4 |
| N-(2-cyanoethyl)-4-ethylcarbanilic acid-(3-(methoxycarbonylamino)-phenyl)-ester | 4 | 4 | 4 | 4 |
| N-(2-cyanoethyl)-3-chloro-4-methylcarbanilic acid-(3-(methoxycarbonylamino)-phenyl)-ester | 4 | 4 | 4 | 4 |
| N-(2-cyanoethyl)-4-bromo-carbanilic acid-(3-(methoxycarbonylamino)-phenyl)-ester | 4 | 4 | 4 | 4 |
| 4-ethyl-N-(2-cyanoethyl)-carbanilic acid-[3-(ethoxycarbonylamino)-phenyl]-ester | 4 | 4 | 4 | 4 |
| N-(2-cyanoethyl)-3-methoxycarbanilic acid-[3-(ethoxycarbonylamino)-phenyl]-ester | — | — | 4 | — |
| N-(2-cyanoethyl)-3-chloro-4-methylcarbanilic acid-[3-(methylcarbonylamino)-phenyl]-ester | — | — | 4 | 4 |
| N-(2-cyanoethyl)-4-methylcarbanilic acid-[3-(2-methylpropoxycarbon- | | | | |

TABLE I-continued

| Compound | Application Preemergence Sinapis/Solanum | | Application Postemergence Sinapis/Solanum | |
| --- | --- | --- | --- | --- |
| ylamino)-phenyl]-ester | — | — | 4 | — |
| N-(2-cyanoethyl)-carbanilic acid-[3-(2-chloro-1-methylethoxycarbonylamino)-phenyl]-ester | — | — | 4 | 4 |
| N-(2-cyanoethyl)-carbanilic acid]-[3-(n-propoxycarbonylamino)-phenyl]-ester | 4 | — | 4 | 4 |
| N-(2-cyanoethyl)-3-methoxycarbanilic acid-[3-(methylthiocarbonylamino)-phenyl]-ester | — | — | 4 | 4 |
| N-(2-cyanoethyl)-3-methylcarbanilic acid-[3-(methoxycarbonylamino)-phenyl]-ester | 4 | 4 | 4 | 4 |
| N-(2-cyanoethyl)-4-ethylcarbanilic acid-[3-(allylcarbonylamino)-phenyl]-ester | — | — | 4 | 4 |
| N-(2-cyanoethyl)-4-ethylcarbanilic acid-[3-butoxycarbonylamino)-phenyl]-ester | — | — | 4 | — |
| N-(2-cyanoethyl)-carbanilic acid-[3-(methoxy-ethoxycarbonylamino)-phenyl]-ester | — | — | 4 | 3 |
| 3-chloro-N-(2-cyanoethyl)-4-methyl-carbanilic acid-[3-(ethoxycarbonylamino)-phenyl]-ester | — | — | 4 | — |
| N-(2-cyanoethyl)-3-methoxycarbanilic acid-[3-(allyloxycarbonylamino)-phenyl]-ester | — | — | 4 | 3 |
| N-(2-cyanoethyl)-4-methylcarbanilic acid-(3-(methoxycarbonylamino)-phenyl]-ester | — | — | 4 | — |
| N-(2-cyanoethyl)-4-methylcarbanilic acid-[3-(2-propinyloxycarbonylamino)-phenyl]-ester | — | — | 4 | 3 |
| N-(2-cyanoethyl)-4-methylcarbanilic acid-[3-(isopropoxycarbonylamino)-phenyl]-ester | — | — | 4 | — |
| N-cyanomethyl)-3-methylcarbanilic acid-[3-(methoxycarbonylamino)-phenyl]-ester | — | — | 4 | 4 |
| N-cyanomethyl-3-methylcarbanilic acid-[3-(ethoxycarbonylamino)-phenyl]-ester | — | — | 4 | 4 |
| N-(2-cyanoethyl)-4-methylcarbanilic acid-[3-(sec-butyloxycarbonylamino)-phenyl]-ester | — | — | 4 | 4 |
| 3-chloro-N-(2-cyanoethyl)-carbanilic acid-[3-(methoxycarbonylamino)-phenyl]-ester | 4 | 4 | 4 | 4 |
| N-cyanomethyl-3-methylcarbanilic acid-[3-(isopropoxycarbonylamino)-phenyl]-ester | — | — | 4 | — |
| N-cyanomethyl-3-methylcarbanilic acid-[3-(2-propinyloxycarbonylamino)-phenyl]-ester | — | — | 4 | 4 |
| 4-ethyl-N-(2-cyanoethyl)-carbanilic acid-[3-(methoxycarbonylamino)-phenyl]-ester | 4 | — | 4 | 4 |
| N-cyanomethyl-2,3-dimethylcarbanilic acid-[3-(methoxycarbonylamino)-phenyl]-ester | — | — | 4 | 4 |
| N-cyanomethyl-3,4-dimethylcarbanilic acid-[3-(methoxycarbonylamino)-phenyl]-ester | — | — | 4 | 3 |
| N-cyanomethyl-3,5-dimethylcarbanilic acid-[3-(methoxycarbonylamino)-phenyl]-ester | — | — | 3 | 3 |

EXAMPLE B

The plants listed below in Table 2 were treated in a hothouse in preemergence application with the compound of the invention stated below in an amount of 3 kg of active agent per about 2.5 acres.

The comparison compound is likewise listed in the Table. The plants were in the growing stage. The compounds were applied in the form of emulsions. The amount of liquid applied was equivalent to 500 liters per about 2.5 acres.

After 2 weeks the results were evaluated on a scale from 0 = total destruction, to 10 = no injury to the plants.

The results in the following Table show clearly the high compatibility and activity of the compounds of the invention, while on the other hand the prior art comparison compound had no herbicidal effect.

TABLE II

| Compound of the invention | kg/ 2.5 acres | Cotton | Brassica | Allium | Madicago | Phaseolus | Arachis | Halianthus | Solanum | Triticum | Hordeum | Stellaria m. | Senecia v. | Matricoria ch. |
| --- | --- | --- | --- | --- | --- | --- | --- | --- | --- | --- | --- | --- | --- | --- |
| N-(2-cyanoethyl)-carbanilic acid | 3 | 10 | 0 | 0 | 0 | 0 | 0 | 0 | 0 | 1 | 0 | 0 | 0 | 0 |

TABLE II-continued

| Compound of the invention | kg/ 2.5 acres | Lam- ium a. | Cent- aurea c. | Amaran- thus t. | Gal- ium a. | Chrysan- themum s. | Ipo- mea a. | Poly- gonum l. | Ave- na f. | Alope- corus m. | Digit- aria s. | Sorg- hum h. | Poa a. |
|---|---|---|---|---|---|---|---|---|---|---|---|---|---|
| N-(2-cyanoethyl)-carbanilic acid (3-(methoxycarbonylamino)-phenyl)-ester | 3 | 0 | 0 | 0 | 0 | 0 | 0 | 0 | 0 | 0 | 0 | 0 | 0 |
| Comparison Compound 3-(methoxycarbonyl-aminophenyl)-N-(3-methylphenyl)-carbamate | 3 | 10 | 10 | 10 | 10 | 10 | 10 | 10 | 10 | 10 | 10 | 10 | 10 |
| Untreated | — | 10 | 10 | 10 | 10 | 10 | 10 | 10 | 10 | 10 | 10 | 10 | 10 |

TABLE III

| Compound of the invention | kg/ 2.5 Acres | Baum- wolle | Bras- sico | Al- lium | Cu- cumie | Medi- cago | Halian- thus | Sola- num | Trit- icum | Hord- eum | Stel- laria m. | Sene- cia v. | Matric- aria ch. | Lam- ium a. |
|---|---|---|---|---|---|---|---|---|---|---|---|---|---|---|
| N-(2-Cyanethyl)-carbanilic acid (3-(methoxycarbonylamino)-phenyl)-ester | 3 | 10 | 0 | 0 | 0 | 0 | 0 | 0 | 0 | 0 | 0 | 0 | 0 | 0 |
| Comparison Compound 3-(Methoxycarbonylaminophenyl)-N-(3-methylphenyl)-carbamate | 3 | 0 | 0 | 0 | 0 | 0 | 0 | 0 | 0 | 0 | 0 | 0 | 4 | 0 |
| Untreated | — | 10 | 10 | 10 | 10 | 10 | 10 | 10 | 10 | 10 | 10 | 10 | 10 | 10 |

| Compound of the invention | kg/ 2.5 Acres | Cent- aurea c. | Amaran- thus r. | Gal- ium a. | Chrysan- themum s. | Ipo- mea p. | Poly- gonum l. | Ave- na f. | Alope- curos m. | Echin- ochloa c.g. | Digit- aria s. | Sorg- hum h. | Poa a. |
|---|---|---|---|---|---|---|---|---|---|---|---|---|---|
| N-(2-Cyanethyl)-carbanilic acid (3-(methoxycarbonylamino)-phenyl)-ester | 3 | 0 | 0 | 0 | 0 | 0 | 0 | 0 | 0 | 0 | 0 | 0 | 0 |
| Comparison Compound 3-(Methoxycarbonylaminophenyl)-N-(3-methylphenyl)-carbamate | 3 | 0 | 5 | 0 | 0 | 0 | 0 | 7 | 8 | 10 | 4 | 8 | 3 |
| Untreated | — | 10 | 10 | 10 | 10 | 10 | 10 | 10 | 10 | 10 | 10 | 10 | 10 |

EXAMPLE C

The plants listed below in Table 3 were treated in a hothouse in a postemergence application with the compound of the invention indicated in the Table in an amount of 3 kg of active agent per about 2.5 acres. The comparison compound is also indicated in the Table.

The plants were in the growing stage. The compounds were applied as emulsions. The amount of liquid applied corresponded to 500 liters per about 2.5 acres.

The results were evaluated after 2 weeks on a scale from 0 = total destruction, to 10 = no injury to the plant.

The results obtained according to Table 3 clearly show the high compatibility of the compounds of the invention while the comparison compound destroyed the agriculturally valuable plants and had a lower breadth of spectrum of herbicidal activity.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. Carbanilic acid ester of the formula

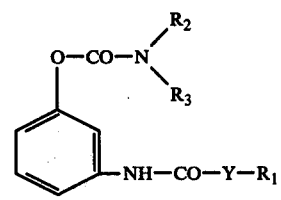

in which $R_1$ is alkyl of 1 to 6 carbon atoms, alkenyl of 2 to 6 carbon atoms or alkinyl of 2 to 6 carbon atoms, $R_2$ is cyanoalkyl of 1 to 4 carbon atoms in the alkyl group, $R_3$ is phenyl which may also be substituted in one or two places by the same or different groups selected from the group of alkyl of 1 to 6 carbon atoms, alkoxy of 1 to 5 carbon atoms, alkylthio of 1 to 3 carbon atoms, halogen and trifluoromethyl, and Y is oxygen or sulfur.

2. The compound of claim 1 which is N-(2-cyanoethyl)-carbanilic acid-(3-(methoxycarbonylamino)-phenyl)-ester.

3. The compound of claim 1 which is N-cyanomethylcarbanilic acid-(3-(methoxycarbonylamino)-phenyl)-ester.

4. The compound of claim 1 which is N-(2-cyanoethyl)-carbanilic acid-(3-(ethoxycarbonylamino)-phenyl)-ester.

5. The compound of claim 1 which is N-cyanomethylcarbanilic acid-(3-(ethoxycarbonylamino)-phenyl)-ester.

6. The compound of claim 1 which is N-(2-cyanoethyl)-carbanilic acid-(3-(1-methylethoxycarbonylamino)-phenyl)-ester.

7. The compound of claim 1 which is N-cyanomethylcarbanilic acid-(3-(1-methylethoxycarbonylamino)-phenyl)-ester.

8. The compound of claim 1 which is N-cyanomethylcarbanilic acid-(3-methylthiocarbonylamino)-phenyl)-ester.

9. The compound of claim 1 which is N-(2-cyanoethyl)-carbanilic acid-(3-(methylthiocarbonylamino)-phenyl)-ester.

10. The compound of claim 1 which is N-(2-cyanoethyl)-carbanilic acid-(3-(1-methylpropoxycarbonylamino)-phenyl)-ester.

11. The compound of claim 1 which is N-cyanomethyl-3-trifluoromethylcarbanilic acid-(3-(methoxycarbonylamino)-phenyl)-ester.

12. The compound of claim 1 which is N-(2-cyanoethyl)-carbanilic acid-(3-(allyloxycarbonylamino)-phenyl)-ester.

13. The compound of claim 1 which is N-(2-cyanoethyl)-carbanilic acid-(3-(2-propinyloxycarbonylamino)-phenyl)-ester.

14. The compound of claim 1 which is N-(2-cyanoethyl)-3-methoxycarbanilic acid-(3-(methoxycarbonylamino)-phenyl)-ester.

15. The compound of claim 1 which is N-cyanomethyl-3,5-dichlorocarbanilic acid-(3-(methoxycarbonylamino)-phenyl)-ester.

16. The compound of claim 1 which is N-cyanomethyl-3,4-dichlorocarbanilic acid-(3-methoxycarbonylamino)-phenyl)-ester.

17. The compound of claim 1 which is N-(2-cyanoethyl)-4-ethylcarbanilic acid-(3-(methoxycarbonylamino)-phenyl)-ester.

18. The compound of claim 1 which is N-(2-cyanoethyl)-3-chloro-4-methylcarbanilic acid-(3-(methoxycarbonylamino)-phenyl)-ester.

19. The compound of claim 1 which is N-(2-cyanoethyl)-4-bromocarbanilic acid-(3-(methoxycarbonylamino)-phenyl)-ester.

20. The compound of claim 1 which is 4-ethyl-N-(2-cyanoethyl)-carbanilic acid-[3-ethoxycarbonylamino)-phenyl]-ester.

21. The compound of claim 1 which is N-(2-cyanoethyl)-3-methoxycarbanilic acid-[3-(ethoxycarbonylamino)-phenyl]-ester.

22. The compound of claim 1 which is N-(2-cyanoethyl)-carbanilic acid-[3-(2-chloro-1-methylethoxycarbonylamino)-phenyl]-ester.

23. The compound of claim 1 which is N-(2-cyanoethyl)-carbanilic acid-[3-(n-propoxycarbonylamino)-phenyl]-ester.

24. The compound of claim 1 which is N-(2-cyanoethyl)-4-ethylcarbanilic acid-[3-(2-methoxyethoxycarbonylamino)-phenyl]-ester.

25. The compound of claim 1 which is N-(2-cyanoethyl)-3-methoxycarbanilic acid-[3-(1-methylethoxycarbonylamino)-phenyl]-ester.

26. The compound of claim 1 which is 4-ethyl-N-(2-cyanoethyl)-carbanilic acid-[3-(isopropoxycarbonylamino)-phenyl]-ester.

27. The compound of claim 1 which is N-(2-cyanoethyl)-2-methoxycarbanilic acid-[3-(methoxycarbonylamino)-phenyl]-ester.

28. The compound of claim 1 which is N-(2-cyanoethyl)-4-ethylcarbanilic acid-[3-(butoxycarbonylamino)-phenyl]-ester.

29. The compound of claim 1 which is N-(2-cyanoethyl)-3-methoxycarbanilic acid-[3-(methylthiocarbonylamino)-phenyl]-ester.

30. The compound of claim 1 which is N-(2-cyanoethyl)-3-methylcarbanilic acid-[3-(methoxycarbonylamino)-phenyl]-ester.

31. The compound of claim 1 which is N-(2-cyanoethyl)-carbanilic acid-[3-(2-chloro-1-methylethoxycarbonylamino)-phenyl]-ester.

32. The compound of claim 1 which is N-(2-cyanoethyl)-carbanilic acid-[3-(methoxy-ethoxycarbonylamino)-phenyl]-ester.

33. The compound of claim 1 which is 3-chloro-N-(2-cyanoethyl)-4-methylcarbanilic acid-[3-(ethoxycarbonylamino)-phenyl]-ester.

34. The compound of claim 1 which is N-(2-cyanoethyl)-3-methoxycarbanilic acid-[3-(allyloxycarbonylamino)-phenyl]-ester.

35. The compound of claim 1 which is N-(2-cyanoethyl)-4-methylcarbanilic acid-[3-(2-propinyloxycarbonylamino)-phenyl]-ester.

36. The compound of claim 1 which is N-(2-cyanoethyl)-4-methylcarbanilic acid-[3-(isopropoxycarbonylamino)-phenyl]-ester.

37. The compound of claim 1 which is N-(2-cyanoethyl)-3-methoxycarbanilic acid-[3-(2-propinyloxycarbonylamino)-phenyl]-ester.

38. The compound of claim 1 which is N-cyanomethyl-3-methylcarbanilic acid-[3-methoxycarbonylamino)-phenyl]-ester.

39. The compound of claim 1 which is N-(2-cyanoethyl)-3-methoxycarbanilic acid-[3-(2-methoxyethoxycarbonylamino)-phenyl]-ester.

40. The compound of claim 1 which is N-cyanomethyl-3-methylcarbanilic acid-[3-ethoxycarbonylamino)-phenyl]-ester.

41. The compound of claim 1 which is N-(2-cyanoethyl)-4-methylcarbanilic acid-[3-(sek-butyloxycarbonylamino)-phenyl]-ester.

42. The compound of claim 1 which is 3-chloro-N-(2-cyanoethylcarbanilic acid-[3-(methoxycarbonylamino)-phenyl]-ester.

43. The compound of claim 1 which is N-cyanomethyl-2,6-dimethylcarbanilic acid-[3-(methoxycarbonylamino)-phenyl]-ester.

44. The compound of claim 1 which is N-cyanomethyl-2,6-dimethylcarbanilic acid-[3-(ethoxycarbonylamino)-phenyl]-ester.

45. The compound of claim 1 which is N-cyanomethyl-3-methylcarbanilic acid-[3-isopropoxycarbonylamino)-phenyl]-ester.

46. The compound of claim 1 which is N-cyanomethyl-3methylcarbanilic acid-[3-(2-propinyloxycarbonylamino)-phenyl]-ester.

47. The compound of claim 1 which is 4-ethyl-N-(2-cyanoethyl)-carbanilic acid-[3-(methoxycarbonylamino)-phenyl]-ester.

48. The compound of claim 1 which is N-cyanomethyl-2,3-dimethyl-carbanilic acid-[3-(methoxycarbonylamino)-phenyl]-ester.

49. The compound of claim 1 which is N-cyanomethyl-3,4-dimethylcarbanilic acid-[3-(methoxycarbonylamino)-phenyl]-ester.

50. The compound of claim 1 which is N-cyanomethyl-3,5-dimethylcarbanilic acid-[3-(methoxycarbonylamino)-phenyl]-ester.

51. The compound of claim 1 which is N-(2-cyanoethyl)-4-methylcarbanilic acid-[3-(2-methylpropoxycarbonylamino)-phenyl]-ester.

52. A herbicidal composition comprising about 10 to 80% by weight of at least one active agent according to claim 1, and about 90 to 20% by weight of a liquid or solid carrier material.

53. The herbicidal composition of claim 52 which includes up to 20% by weight of a surface active agent.

54. The herbicidal composition of claim 52 wherein the surface active agent is present at a ratio of said active agent to surface active agent of between 1:10 and 1:0.4.

55. A process of selectively suppressing or reducing the growth of weeds in cotton plantations wherein the composition of claim 52 is applied in an amount of between 100 and 1000 liters per about 2.5 acres of aqueous suspension of the herbicidal composition of claim 52.

* * * * *